United States Patent [19]
Mangiardi et al.

[11] Patent Number: 5,665,092
[45] Date of Patent: Sep. 9, 1997

[54] MARKER FOR SURGICAL PROCEDURES

[76] Inventors: John R. Mangiardi, 988 Fifth Ave., New York, N.Y. 10021; Franklin G. Moser, 1601 Rising Glen Rd., Los Angeles, Calif. 90069; Allen B. Kantrowitz, 23 Woodland Pl., Chappaqua, N.Y. 10514; Karl Leibinger, Reutestrasse 3, 79100 Freiburg-Günterstal; Franz Leibinger, Roethestrasse 38, 79312 Emmendingen, both of Germany

[21] Appl. No.: 566,275

[22] Filed: Dec. 1, 1995

Related U.S. Application Data

[63] Continuation of Ser. No. 202,926, Feb. 28, 1994, abandoned.

[30] Foreign Application Priority Data

Mar. 1, 1995 [DE] Germany ............ 43 06 277.6

[51] Int. Cl.$^6$ ..................................... A61B 17/56
[52] U.S. Cl. ........................ 606/86; 604/104; 604/73
[58] Field of Search .................. 606/104, 73, 72, 606/75, 76, 86, 117, 185, 228, 224, 232; 604/165

[56] References Cited

U.S. PATENT DOCUMENTS

| | | | |
|---|---|---|---|
| 4,252,110 | 2/1981 | Behney | 606/86 |
| 4,738,255 | 4/1988 | Goble et al. | 606/86 |
| 4,774,948 | 10/1988 | Markham . | |
| 4,799,495 | 1/1989 | Hawkins et al. . | |
| 4,986,279 | 1/1991 | O'Neill . | |
| 5,018,530 | 5/1991 | Rank et al. . | |
| 5,053,046 | 10/1991 | Janese . | |
| 5,059,197 | 10/1991 | Urie et al. . | |
| 5,127,916 | 7/1992 | Spencer et al. . | |
| 5,141,520 | 8/1992 | Goble et al. | 606/104 |
| 5,178,164 | 1/1993 | Allen . | |
| 5,201,760 | 4/1993 | West | 606/224 |
| 5,207,679 | 5/1993 | Li | 606/232 |
| 5,258,016 | 11/1993 | DiPoto et al. | 606/104 |
| 5,279,570 | 1/1994 | Dombrowski et al. | 604/615 |

FOREIGN PATENT DOCUMENTS 4216694 12/1992 Germany .

OTHER PUBLICATIONS

Needle Localization for Lateral Facetectomies for Cervical Disc Surgery, by F.G. Moser, E. Morton, J. Mangiardi, L. Rothman, Proceedings of the Association of University Radiologists Annual Meeting Apr. 12–26, 1992, p. 1119 (P31).

*Primary Examiner*—Guy V. Tucker
*Attorney, Agent, or Firm*—Martin A. Farber

[57] ABSTRACT

A marker for surgical procedures which permits an operating surgeon to mark the place to be operated on accurately in a manner which is as free of pain as possible for the patient, and has a tubular guide cannula (1), an introduction tube (2), and a marking pin (3) which is connected to a flexible bar (4), the bar (4) being adapted to be introduced into the introduction tube (2) from its proximal end (5) by such an amount that it protrudes at the distal end (6) of the introduction tube (2). The marking pin (3) can be supported on the proximal end (5) of the introduction tube (2). The introduction tube (2) with the bar (4) therein and the attached marking pin (3) can be introduced via the distal end (8) of the guide cannula (1) into the latter by such an amount that the proximal end (5) of the introduction tube (2) is located in the region of the proximal end (7) of the guide cannula (1), and the marking pin (3) extends out of the proximal end (7) of the guide cannula (1).

40 Claims, 7 Drawing Sheets

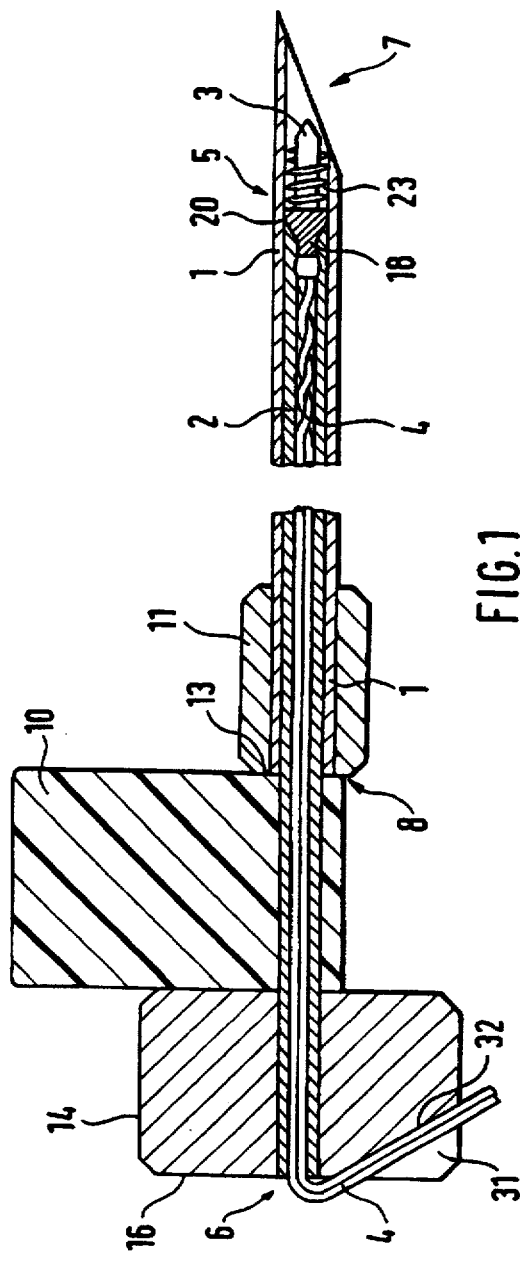
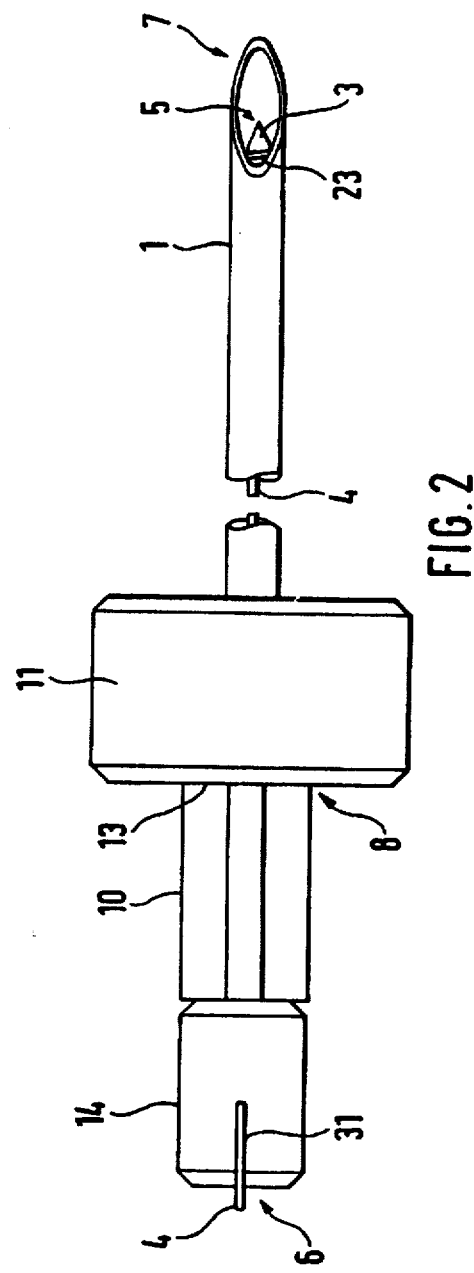
FIG.1
FIG.2

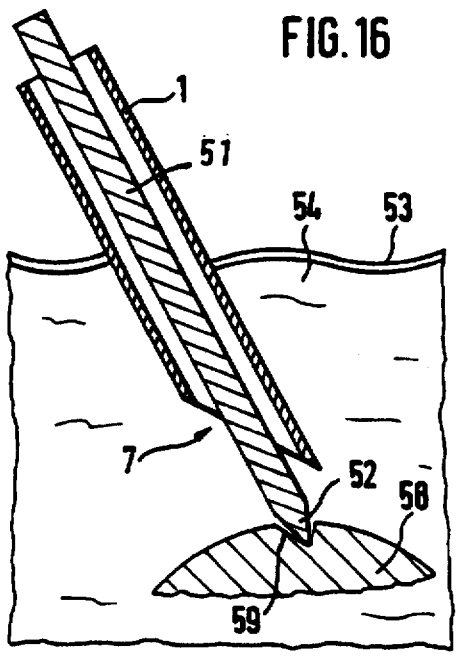
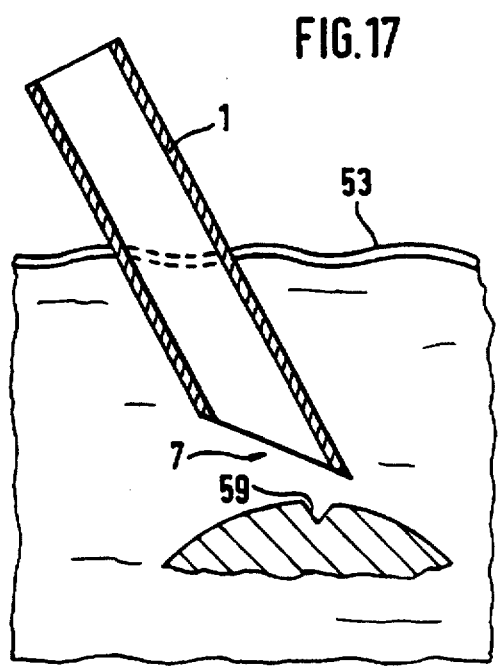
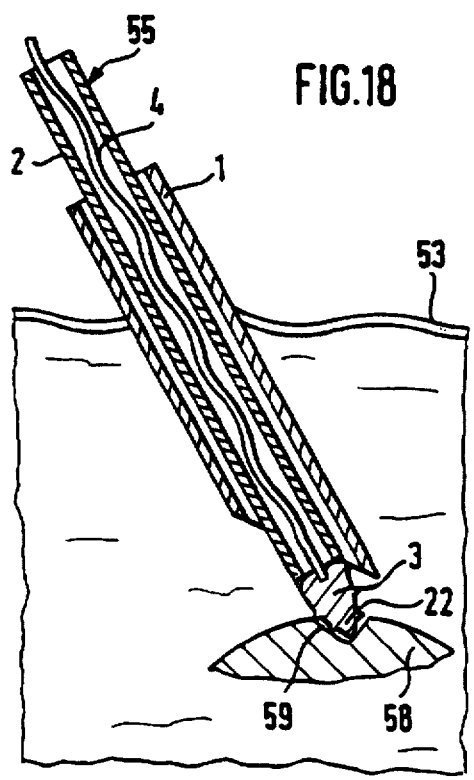
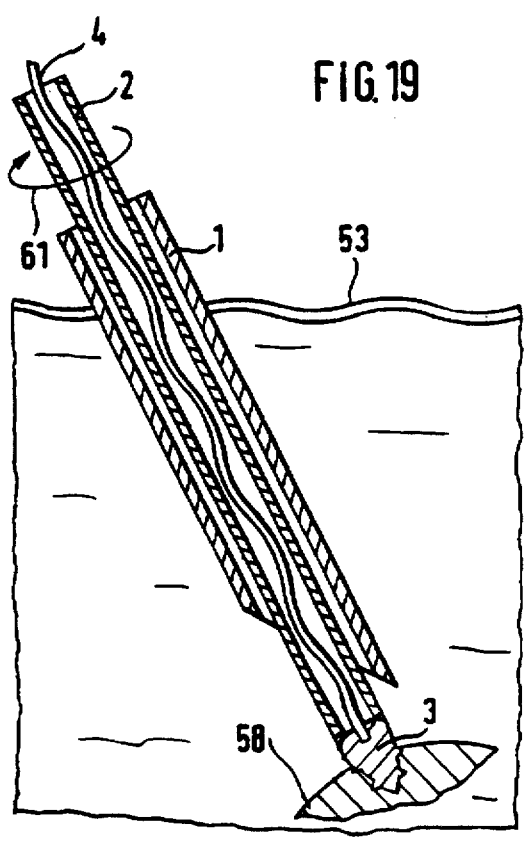

MARKER FOR SURGICAL PROCEDURES

RELATED APPLICATION

This application is a continuation of our application Ser. No. 08/202,926 filed Feb. 28, 1994, now abandoned.

FIELD AND BACKGROUND OF THE INVENTION

The present invention relates to a marker for surgical procedures.

In carrying out surgical procedures on complicated bone parts within the human body, for instance the spinal column, the place where the operation is to be carried out is determined and established prior to the operation. In order to avoid having surgical intervention taking place too far from the place to be operated on, or at the wrong angle or in the wrong plane, it is necessary to mark this place as accurately as possible.

The marking needles used up to the present time can be positioned and fixed only with inadequate precision. Even colored marking of the corresponding place on the skin is too inaccurate, since the part of the skin in question can move when the patient is placed on the operating table.

A situation of interest is a particular type of surgical operation, namely a facetectomy for a posterior-lateral approach to a cervical discectomy. This operation is made difficult by the inability to be assured of the correct location of the discectomy. Because of this, a large incision and intraoperative x-rays were required. There is a need to pinpoint the correct location and allow a much smaller incision. This must be accomplished in a manner wherein any movement of the muscles of the neck relative to the spine would not diminish accuracy in the marking of the location.

SUMMARY OF THE INVENTION

The object of the present invention is therefore to provide a marker for surgical procedures which permits the operating physician to effect a precise marking of the place to be operated on by a procedure which is as free of pain as possible for the patient.

For this purpose, the marker for surgical procedures of the invention is inserted into the patient by means of a tubular assembly and a tubular guide cannula, the tubular assembly comprising an introduction tube constructed as a hollow stylet, and a marking pin which is attached to a flexible bar. The bar is adapted to be introduced from the proximal end of the introduction tube and to extend through the latter to protrude at the distal end of the introduction tube. The marking pin is supported on the proximal end of the introduction tube. The tubular assembly is formed of the introduction tube, with the bar which is introduced into it and the marking pin. The tubular assembly is introduced into the distal end of the guide cannula a sufficient distance so as to bring the proximal end of the introduction tube adjacent the proximal end of the guide cannula, and with the marking pin protruding from the proximal end of the guide cannula.

Prior to the insertion of the tubular assembly into the patient, the patient is prepared in sterile fashion. A solid stylet is inserted into the guide cannula with the cutting tip of the stylet located adjacent the proximal end of the guide cannula. The combination of cannula and stylet is inserted through the skin under local anesthesia, and pushed to the operative site, preferably under guidance of fluoroscopy. The stylet is then pressed against the bone to produce a score on the bone, the score serving as a guide to facilitate a subsequent step of the procedure, an attachment of the marking pin to the bone at the site of the score.

After completion of the scoring, the guide cannula is held in its position while the stylet is withdrawn from the guide cannula. The introduction tube (constructed as a hollow stylet) with the marking pin therein are inserted into the guide cannula to bring the tip of the marking pin into contact with the bone at the site of the score. Thereby, the tubular assembly has been inserted into its operative position to enable attachment of the marking pin to the bone. It is noted that the orientation of the guide cannula as well as of the entire tubular assembly is equal, preferably, to the angle of approach which a surgeon is to use in a subsequent surgical procedure.

The marking pin is then advanced into the bone by turning the introduction tube thereby screwing the marking pin into the bone. The guide cannula and the introduction tube are now pulled back over the bar. The bar remains in its operative position and extends out of the patient's skin. Since the marking pin is seated firmly in the bone, the bar protruding from the operative position provides the surgeon with a reliable indication as to where or at what angle the intervention on the bone in question is to take place.

In a preferred embodiment of the invention, a handle by which the guide cannula can be manually guided is present on the distal end of the guide cannula, away from the patient. The handle of the guide cannula has substantially the shape of a right parallelepiped, as a result of which a dependable, sensitive guidance by thumb and index finger or by suitable forceps is possible. The shape of the handle can possibly also be round, barreled, or the like and it may have a knurled or fluted surface.

Similarly, there is preferably provided on the distal end of the introduction tube, a handle by which the introduction tube can be guided and rotated around its longitudinal axis. Here, also, the important factor is that a dependable, sensitive guidance by thumb and index finger or by suitable forceps be possible. For this purpose, the handle of the introduction tube has substantially the shape of a right parallelepiped corresponding to the shape of the handle of the guide cannula. Here, also, the shape of the handle may also possibly be round, barreled, or the like and it may have a knurled or fluted surface.

In order, upon the introduction of the surgical marker, to be certain that the marking pin always remains inside the proximal end of the guide cannula, in a preferred embodiment, a spacer can be arranged in the region of the distal end of the introduction tube for limiting a maximum depth of insertion of the introduction tube into the guide cannula. Thereby, with the spacer applied, the marker does not extend out of the proximal end of the guide cannula.

In a preferred embodiment of the surgical marker, the marking pin is arranged, fixed in rotation, at the proximal end of the introduction tube. Furthermore, the marking pin is tapered down towards its free end and has on its outer surface, at least in sections thereof, at least one screw thread. In this way, the marking pin can be screwed into the bone at the desired place by rotating the introduction tube. This assures a reliable immovable marking of the place of operation.

There are a number of possibilities for connecting the marking pin to the bar. In a preferred embodiment of the invention, the marking pin is provided on its distal end with a flattened region which has an opening passing radially through it. The bar is preferably developed as an implantation wire helix which is held securely in the opening by, for instance, twisting the ends of two wires of the helix.

In another embodiment, the marking pin is provided on its distal end with a flattened region which has an axial blind hole in its center. In this case, the bar is formed of implantation wire which is held securely in the blind hole, for instance by crimping the distal end of the pin, welding or the like.

In a further embodiment, the marking pin has a region of X-shaped cross section at its distal end, provided at its center with an axial blind hole. In this case, also, the rod is developed as implantation wire which is held securely in the blind hole.

The above-described developments of the marking pin serve for the purpose that the marking pin can be attached, detachably, and fixed in rotation to the proximal end of the introduction tube. For this purpose, the introduction tube is provided at its proximal end with two radial recesses which are open at the edge and in which the flattened regions of the marking pin can be received, at least partially fixed for rotation. For the region of the marking pin of X-shaped cross section, four recesses which are open on the edge are provided, uniformly distributed over the circumference of the introduction tube. Of course, three or else some other number of recesses which are open on the edge and corresponding engagement parts on the marking pin are possible.

In a preferred embodiment, the bar can be detachably fastened at its distal end to the distal end of the introduction tube. If the bar is developed as an implantation wire, this can be achieved in the manner that the handle surrounds the distal end of the introduction tube and has a recess, open on its edge, which extends radially away from the introduction tube and into which the free end of the implantation wire can be placed. By a bending-over and a pulling of the implantation wire into the recess, the wire is tensioned since the marking pin, due to the fact that its outside diameter is greater than the inside dimension of the introduction tube, prevents the implantation wire from being pulled backwards by the introduction tube. This facilitates bringing the surgical marker to the proper place.

The guide cannula, the introduction tube, the marking pin or the bar are preferably made of a material of good X-ray contrast, for instance steel. The marking pin and the bar are in this case preferably made of implantation steel.

Should it turn out that the operation will not be performed although the marking pin has already been screwed within a bone inside the body, the introduction tube can be placed into the guide cannula from the distal end of the latter, and the guide cannula together with the introduction tube can then be pushed over the bar and the implantation wire. As soon as the proximal end of the implantation wire on which the marking pin is fastened has been reached, the introduction tube is pushed over the distal end of the marking pin and turned until the engagement parts on the marking pin have engaged in the recesses on the proximal end of the introduction tube. The introduction tube is then turned by its handle in such a manner that the marking pin is unscrewed from the bone. Thereupon, the guide cannula together with the marking pin and the implantation wire are pulled out.

BRIEF DESCRIPTION OF THE DRAWINGS

Further advantages and embodiments of the object of the invention will be explained in connection with the following description of the accompanying drawings, in which:

FIG. 1 is a diagrammatic cross-sectional view through the surgical marker of the invention, shown in longitudinal direction;

FIG. 2 is a diagrammatic side view of the surgical marker of the invention, seen in longitudinal direction;

FIGS. 16–20 are diagrammatic illustrations of the steps of the method of the invention (not to actual relative proportions and with the handles and other portions omitted for clarity of illustration).

DETAILED DESCRIPTION OF THE PREFERRED EMBODIMENTS

Figure 9:
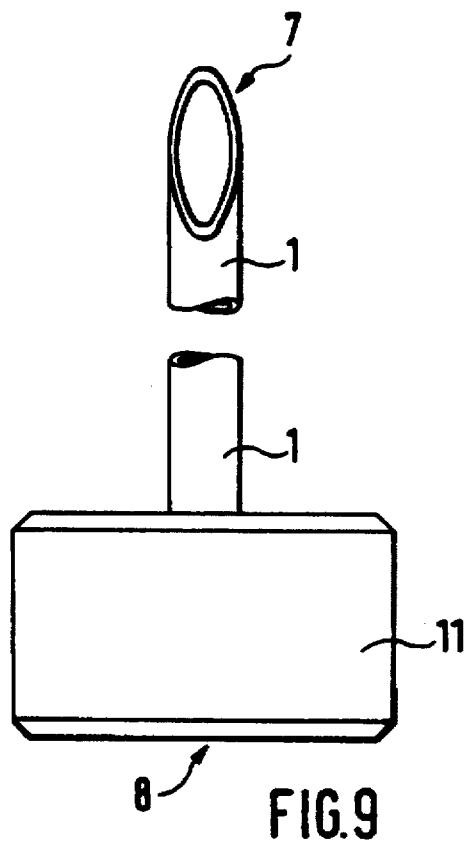
FIG. 9 is a diagrammatic side view of a guide cannula with handle arranged thereon.
Figure 10:
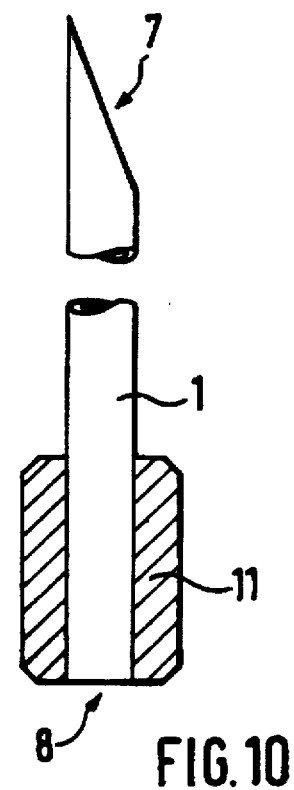
FIG. 10 is a diagrammatic sectional view of the guide cannula with handle arranged thereon in accordance with FIG. 9.
Figure 13:
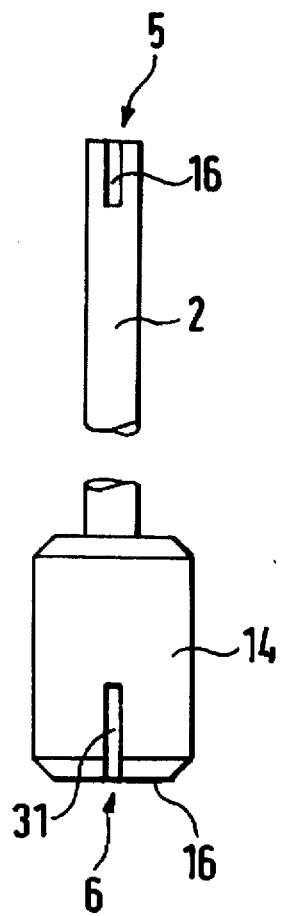
FIG. 13 is a diagrammatic side view of an introduction tube with handle arranged thereon.
Figure 14:
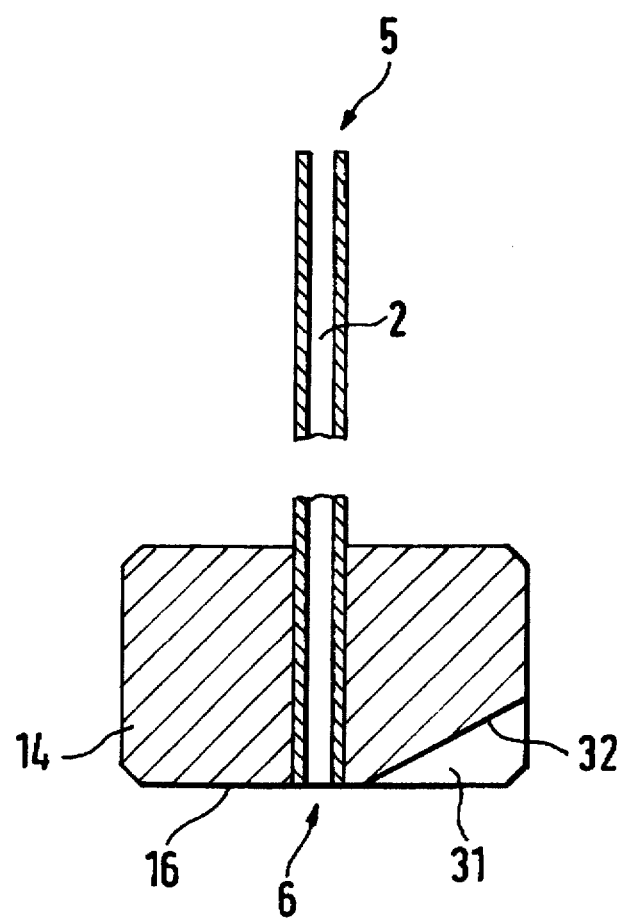
FIG. 14 is a diagrammatic cross-sectional view of the introduction tube with handle arranged thereon, in accordance with FIG. 13.

FIG. 1 shows a surgical marker in accordance with the invention in a diagrammatic cross-section view, while FIG. 2 shows it in a diagrammatic side view in the longitudinal direction. The surgical marker has a guide cannula 1 (FIGS. 1, 9, 10) in the shape of a cylindrical tube, an introduction tube 2 (FIGS. 1, 13, 14) in the shape of a cylindrical tube, and a marking pin 3 includes and which is connected to a flexible bar of implantation wire 4. The guide cannula 1, the introduction tube 2, the marking pin 3 and the bar 4 consist of a material of good X-ray contrast, for instance steel, the marking pin 3 and the rod 4 being preferably made of implantation steel.

The bar 4 can be introduced into the introduction tube 2 from the proximal end 5 of the tube by such an amount that it protrudes at the distal end 6 of the introduction tube and the marking pin 3 can be supported on the proximal end of the introduction tube 2. In this connection, the outer diameter of the marking pin 3 is greater than the inside diameter of the introduction tube 2 but smaller than the inside diameter of the guide cannula 1.

The introduction tube 2 has an outside diameter which is about as large as that of the marking pin 3. Thus, the introduction tube 2 and the marking pin 3 can be introduced together in a sliding seat into the guide cannula 1. The introduction tube 2, together with the bar 4 introduced into it and the marking pin 3, can be introduced from the distal end 8 of the guide cannula 1 so far into the cannula that the proximal end 5 of the introduction tube 2 is located in the region of the proximal end 7 of the guide cannula 1 and the marking pin 3 can extend out of the proximal end of the guide cannula 1. In FIG. 1, the distal end 6 of the introduction tube 2 is pulled out rearwards as compared with the distal end 8 of the guide cannula 1. The distance between the distal end 6 of the introduction tube 2 and the distal end 8 of the guide cannula is determined by a spacer 10 which is placed detachably on the introduction tube 2.

Figure 11:
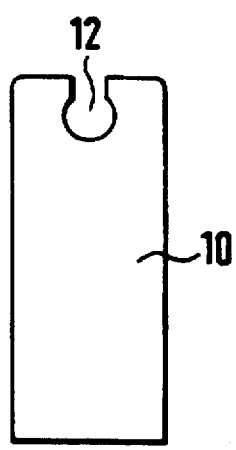
FIG. 11 is a diagrammatic side view of a spacer.
Figure 12:
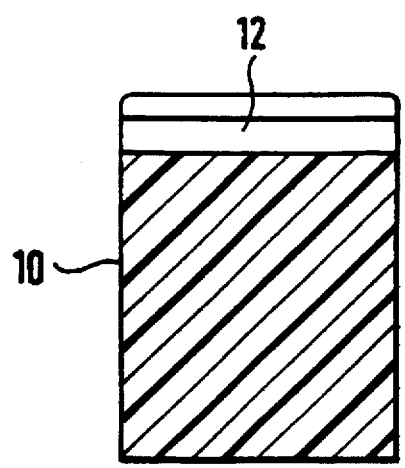
FIG. 12 is a diagrammatic cross-sectional view of the spacer of FIG. 11.

The spacer 10 is made of a plastic, preferably polytetrafluoroethylene, and has the shape approximately of a right parallelepiped (see FIGS. 11, 12), but it may also be of round or barrel shape and have a structured surface. On a narrow side surface of the spacer 10, there is provided a recess 12 which is open at the edge and which has a substantially rectangular shape as seen in cross section. The inside diameter of the widened region corresponds approximately to the outside diameter of the introduction tube 2, while the section closer to the edge has a slightly smaller transverse dimension. Due to the flexibility of the plastic, the spacer 10 can be pushed laterally over the introduction tube 2 and also easily removed again.

The guide cannula 1 is developed as an atraumatic cannula, its proximal end 7 being beveled at an angle of about 20°.

On the distal end 8 of the guide cannula 1 there is provided, fixed in rotation, a handle 11 by which the guide cannula 1 can be manually guided. This handle 11 of the guide cannula 1 has the shape substantially of a right parallelepiped, but it may also be round or of barrel shape and have a structured surface. In this connection, the guide cannula 1 extends through the handle 11 and terminates flush with the distal end surface 13 of the latter.

In the same way, on the distal end 6 of the introduction tube 2 there is arranged a handle 14 by which the introduction tube 2 can be guided and turned around its longitudinal axis. The handle 14 of the introduction tube also is substantially of the shape of a right parallelepiped. In this case, also, the introduction tube 2 extends through the handle 14 and terminates flush with the distal end surface 16 thereof.

The spacer 10 is placed on the introduction tube 2 and lies between the two handles 11 and 14. In this connection, the length of the spacer which determines the distance between the two handles 11 and 14, and thus the depth of the proximal end 5 of the introduction tube 2 in the proximal end 7 of the guide cannula 1, is such that the marking pin 3 is reliably contained within the guide cannula 1 when the spacer 10 is inserted.

In other words, as a result of the spacer 10, the maximum depth of introduction of the introduction tube 2 into the guide cannula 1 is so limited for the period of introduction that, with spacer 10 arranged on the distal end 6 of the introduction tube 2 in front of the handle 14, the marking pin 3 does not protrude out of the proximal end of the guide cannula 1.

The marking pin 3 is so arranged that it can rest, fixed in rotation, on the proximal end 5 of the introduction tube 2. For this purpose, recesses 18 which are open on the edge are developed in the outer surface of the introduction tube 2 at its proximal end 5, corresponding engagement parts 20 (see FIGS. 3 to 6) on the distal end of the marking pin 3 being adapted to engage into said recesses.

Furthermore, the marking pin 3 is tapered at its proximal end so that it terminates in a tip 22. In its central region, the marking pin 3 has several screw threads 23 on its outer surface as well as a polished surface or self-cutting grooves which facilitate the screwing-in. In this way, the marking pin can be screwed at the desired place into the bone by turning the introduction tube 2, in the proximal end 5 of which the marking pin 3 is seated fixed for rotation.

Figure 3:
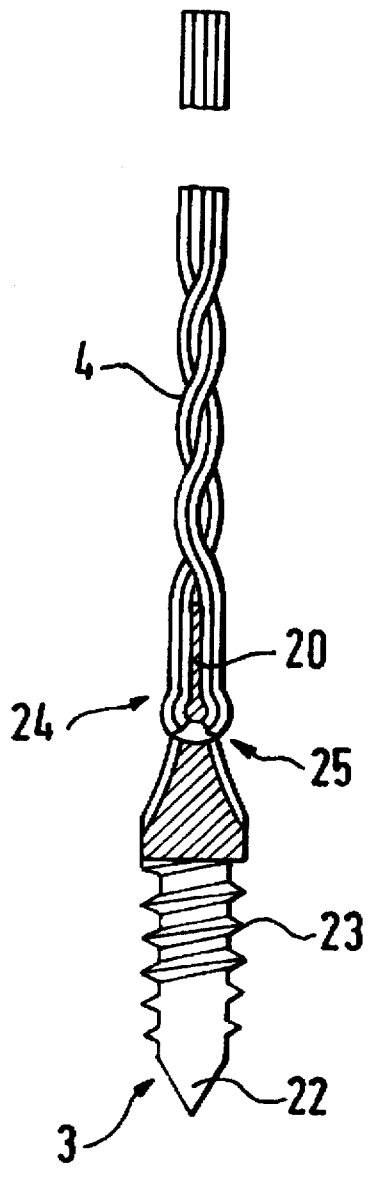
FIG. 3 is a diagrammatic sectional view through a marking pin with the implantation wire present thereon, seen in longitudinal direction in a first embodiment.
Figure 4:
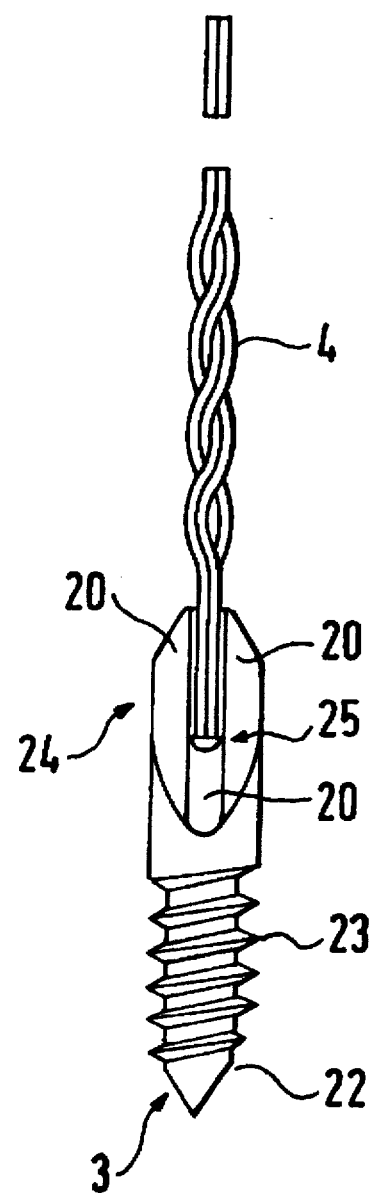
FIG. 4 is a diagrammatic lateral view of the marking pin with the implantation wire present thereon, seen in the longitudinal direction in accordance with FIG. 3.

The marking pin 3 shown in FIGS. 3 and 4 is provided on its distal end with a region which is approximately rectangular in cross section and which has centrally on two longitudinal surfaces two depressions and a radial continuous opening 25. The bar 4 in this embodiment is developed as a double implantation wire helix which is held by twisting securely in the opening. For this purpose, the wire is cut to somewhat more than twice the final dimension of the bar 4 pushed over half its length through the opening 25. The wire is then bent together and twisted or turned to the desired extent.

Figure 6:
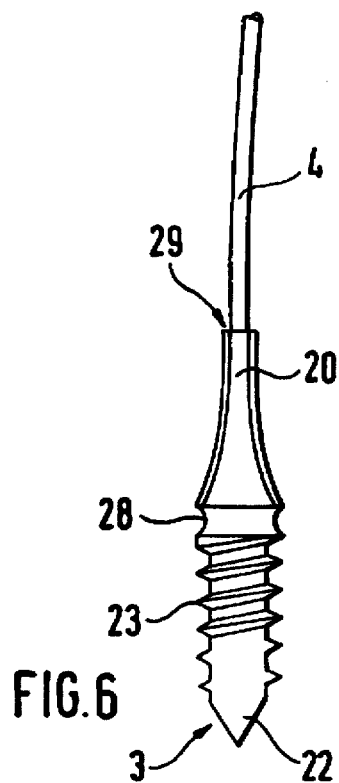
FIG. 6 is a diagrammatic lateral view of the marking pin with the implantation wire present thereon, seen in longitudinal direction, in accordance with FIG. 5.
Figure 5:
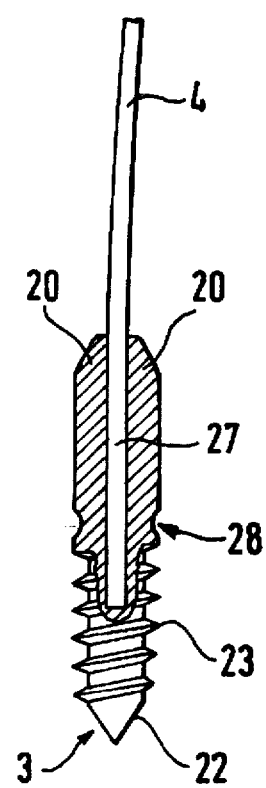
FIG. 5 is a diagrammatic cross-sectional view through a marking pin with implantation wire present thereon, seen in longitudinal direction, in a second embodiment.

In the embodiment shown in FIGS. 5 and 6, the marking pin 3 is provided on its distal end with a flattened region which has centrally a thickening on both sides which has an axial blind hole 27. In this connection the bar is developed as implantation wire 4, which is held securely in the blind hole. For this purpose, the blind hole 27 extends through the central region of the marking pin 3 up to the front section, which is surrounded by the screw thread 23. In the central region of the marking pin 3 the pin has a circumferential depression 28 which is produced by squeezing or crimping, in order to secure the implantation wire in the blind hole 27. In addition to or instead of the crimping, the implantation wire can be welded at the place of emergence 29 from the blind hole 27, for instance by laser welding.

Figure 7:
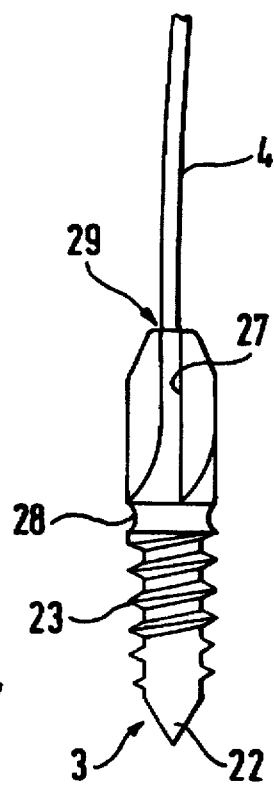
FIG. 7 is a diagrammatic cross-sectional view through a marking pin with the implantation wire present thereon, seen in longitudinal direction in a third embodiment.
Figure 8:
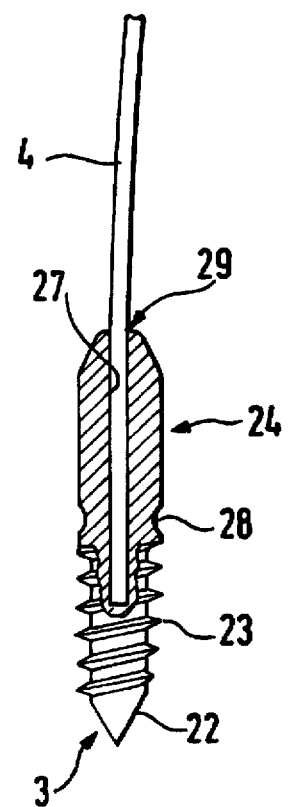
FIG. 8 is a diagrammatic side view of the marking pin with the implantation wire present thereon, seen in longitudinal direction of FIG. 7.

The marking pin 3 shown in FIGS. 7 and 8 is provided at its distal end with a region of X-shape in cross section with an axial blind hole 27 at its center. The bar which is developed as implantation wire 4 is held securely in the blind hole 27. For this purpose the blind hole 27 extends through the central region of the marking pin 3 up to the front section which is surrounded by the screw thread 23. In the central region of the marking pin 3 the pin has a circumferential depression 28 which is produced by squeezing or crimping in order to secure the implantation wire in the blind hole 27. In addition to or instead of the crimping, the implantation wire can be held at the place of emergence 29 from the blind hole 27 by, for instance, laser welding.

The bar 4, or the implantation wire, can be detachably fastened at its distal end to the distal end of the introduction tube. For this purpose, the handle 14 which surrounds the distal end of the introduction tube has a depression 31 (FIGS. 1, 13, 14) open on the edge side which extends radially away from the introduction tube 2 and into which the distal end of the implantation wire 4 can be inserted. The depression 31 is somewhat smaller than the diameter of the implantation wire 4 and is developed in slot shape. The bottom 32 of the depression 31 extends at an angle of about 30° inclined away from the side, in which connection the angle of inclination can also be greater or less than this.

Figure 15:
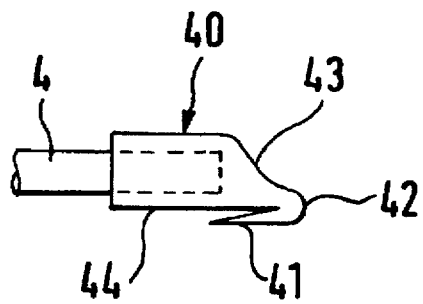
FIG. 15 shows an alternative attachment structure.

FIG. 15 shows an alternative marking pin 40 having a spring loaded barb 41, the spring loading occurring by an elastic tongue 42 of material interconnecting the barb 41 with a base 43 of the pin 40. The pin 40 is attached, as by crimping at 44, to the bar 4. The barb 41 catches upon a small recess (not shown) in the bone at the site of the scoring of the bone.

Referring to FIGS. 16-20, prior to the insertion of tubular assembly 55 (introduction tube 2 releasably connected to the marking pin 3 with the marker bar or wire 4 attached thereto extending through the tube 2) into the patient, the patient is prepared in sterile fashion. Referring first to FIG. 16, a solid, needle stylet 51 is inserted into the guide cannula 1 with the cutting tip 52 of the stylet 51 located adjacent the proximal end 7 of the guide cannula 1. The combination of cannula 1 and stylet 51 is inserted through the patient's skin 53 (i.e. percutaneously) and flesh 54 under local anesthesia, and pushed to the operative site at the angle of approach which a surgeon is to use in a subsequent surgical procedure, preferably under guidance of X-ray fluoroscopy. The stylet 51 is then pressed against the bone 58 to produce a score 59 on the bone, the score serving as a guide to facilitate a subsequent step of the procedure, namely attachment of the marking pin 3 to the bone at the site of the score 59. After completion of the scoring, the guide cannula 1 is held in its position while the stylet 51 is withdrawn from the guide cannula 1 (FIG. 17).

The introduction tube 2 (a hollow stylet) with the marking pin 3 and bar or wire 4 therein (namely the tubular assembly 55) are inserted into the guide cannula 1 to bring the tip 22 of the marking pin 3 into contact with the bone 58 at the site of the score 59 (FIG. 18). In this way the tubular assembly 55 has been inserted into its operative position to enable attachment of the marking pin 3 to the bone 58. It is noted that the orientation of the guide cannula 1 as well as of the tubular assembly 55 is equal, preferably, to the angle of approach which a surgeon is to use in a subsequent surgical procedure.

Figure 20:
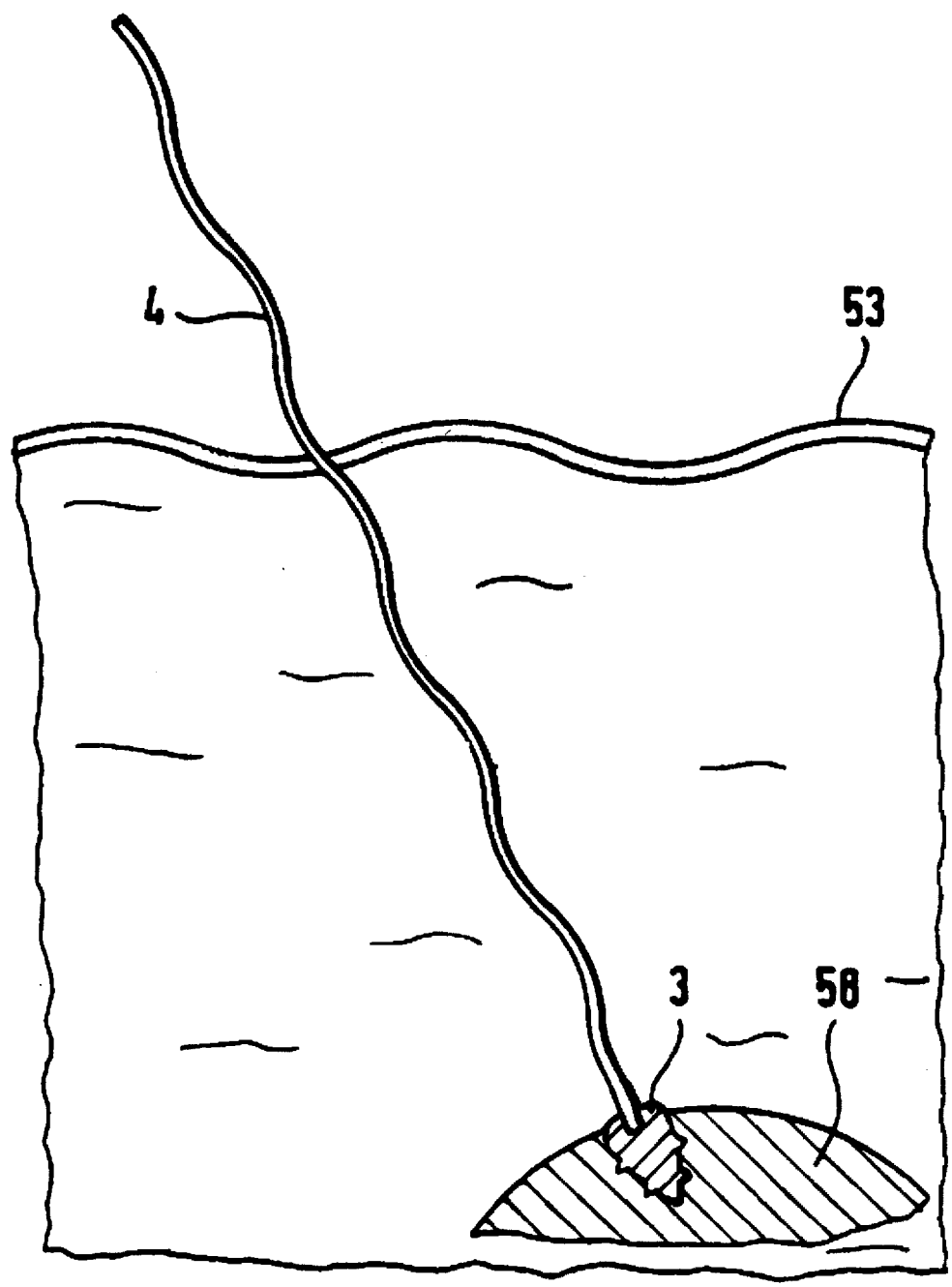

The marking pin 3 is then advanced into the bone, e.g. by turning the tube 2 (as indicated by arrow 61) as a screwdriver whereupon the marking pin becomes affixed to the bone 58 (FIG. 19). The guide cannula 1 and the introduction tube 2 are now pulled back (out) over the bar 4 and removed from the skin 53 and flesh of the patient. The bar or wire 4 remains in its operative position and extends out of the patient's skin 53 (FIG. 20). Since the marking pin 3 is seated firmly in the bone 58, the bar or wire 4 protruding from the operative position will provide the surgeon with a reliable indication as to where and at what angle the intervention on the bone in question is to take place in the operating room.

We claim:

1. A marker of a site on bone for surgical procedures on a patient, comprising
   a tubular guide cannula,
   an introduction tube having a proximal end and a distal end and arranged so as to be insertable within the cannula,
   a flexible bar extending along and being displaceable within the tube, and a marking pin which is attached to a proximal end of the flexible bar and extends beyond the proximal end of the tube;
   wherein the bar protrudes at the distal end of the introduction tube, the introduction tube together with the bar and the marking pin being arranged so as to be inserted into the guide cannula from a distal end of the cannula to place the proximal end of the introduction tube in a region of a proximal end of the guide cannula with the marking pin extending out of the proximal end of the guide cannula, the cannula, introduction tube and marking pin constituting means for positioning and attaching the marking pin to the site on the bone with the bar extending from the pin outwardly through skin and flesh of the patient as a marker of the site for the surgical procedures.

2. A marker for surgical procedures in accordance with claim 1, further comprising means comprising a handle at the distal end of the guide cannula for manually guiding the guide cannula.

3. A marker for surgical procedures according to claim 2, wherein said cannula handle has substantially the shape of a right parallelepiped.

4. A marker for surgical procedures according to claim 1, further comprising a handle at the distal end of said introduction tube enabling the introduction tube to be guided and turned around its longitudinal axis.

5. A marker for surgical procedures according to claim 4, wherein said tube handle has substantially the shape of a right parallelepiped.

6. A marker for surgical procedures according to claim 1, wherein said marking pin is rotatable by a rotation of the introduction tube.

7. A marker for surgical procedures according to claim 1, wherein said marking pin tapers down towards a proximal end thereof.

8. A marker for surgical procedures according to claim 1, wherein said marking pin and said tube are provided with interfacing regions including interlocking surfaces for transmission of rotation from said tube to said pin.

9. A marker for surgical procedures according to claim 8, wherein said marking pin is provided, at least on sections of its outer surface, with at least one screw thread for engagement with the bone of the patient upon rotation of the pin by the introduction tube.

10. A marker for surgical procedures according to claim 9, wherein said screw thread is adapted for securing the marking pin to the bone by screwing attachment.

11. A marker for surgical procedures according to claim 1, wherein the marking pin is provided on a distal end thereof with a flattened region which has an opening passing therethrough, and the bar comprises a double implantation wire helix which is held securely in the opening.

12. A marker for surgical procedures according to claim 1, wherein the marking pin is provided on a distal end thereof with a flattened region which has centrally an axial blind hole, and the bar is formed as an implantation wire which is held securely in the blind hole.

13. A marker for surgical procedures according to claim 1, wherein said marking pin is provided on a distal end thereof with a region of X-shaped cross section which has centrally an axial blind hole, and said bar is formed as an implantation wire which is held securely in the blind hole.

14. A marker for surgical procedures according to claim 14, wherein the proximal end of the introduction tube is provided with at least two radial recesses open on an edge for receiving in engagement the distal end of the marking pin.

15. A marker for surgical procedures according to claim 1, wherein the bar at a distal end thereof is secured releasably to the distal end of the introduction tube.

16. A marker for surgical procedures according to claim 1, wherein at least one of the guide cannula, the introduction tube, the marking pin, and the bar are made from a material having good X-ray contrast.

17. A marker for surgical procedures according to claim 14, wherein said material comprises surgical steel.

18. A marker for surgical procedures according to claim 1, wherein said marking pin is attached to the bar.

19. A marker for surgical procedures according to claim 1, wherein said introduction tube is removable from the marking pin and from the flexible bar.

20. A marker for surgical procedures according to claim 1, wherein said marking pin is releasably attached to the introduction tube.

21. A marker according to claim 1, wherein the introduction tube is provided on said proximal end thereof with at least two radial recesses which are open on an edge for receiving in engagement a distal end of the marking pin.

22. A marker for surgical procedures comprising a tubular guide cannula, an introduction tube having a proximal end and a distal end and arranged so as to be insertable within the cannula, a flexible bar extending along and being displaceable within the tube, and a marking pin which is attached to a proximal end of the flexible bar and extends beyond the proximal end of the tube;

wherein the bar protrudes at the distal end of the introduction tube, the introduction tube together with the bar and the marking pin being arranged so as to be inserted into the guide cannula from a distal end of the cannula to place the proximal end of the introduction tube in the region of a proximal end of the guide cannula with the marking pin extending out of the proximal end of the guide cannula, a handle at the distal end of the introduction tube enabling the introduction tube to be guided and turned around its longitudinal axis, a spacer located between the tube handle and the distal end of the cannula to limit the maximum depth of penetration of the introduction tube into the guide cannula to prevent protrusion of the marking pin out of the proximal end of the guide cannula.

23. The marker according to claim 22, wherein the spacer is detachably connected between the tube handle and the distal end of the cannula.

24. A marker for surgical procedures, comprising a tubular guide cannula, an introduction tube having a proximal end and a distal end and arranged so as to be insertable within the cannula, a flexible bar extending along and being displaceable within the tube, and a marking pin which is attached to a proximal end of the flexible bar and extends beyond the proximal end of the tube;

wherein the bar protrudes at the distal end of the introduction tube, the introduction tube together with the bar and the marking pin being arranged so as to be inserted into the guide cannula from a distal end of the cannula to place the proximal end of the introduction tube in the region of a proximal end of the guide cannula with the marking pin extending out of the proximal end of the guide cannula, wherein the marking pin is provided on a distal end thereof with a flattened region which has an opening passing therethrough, and the bar comprises a double implantation wire helix which is held securely in the opening, and the introduction tube is provided on said proximal end thereof with at least two radial recesses which are open on an edge for receiving the flattened region of the marking pin.

25. A marker for surgical procedures, comprising a tubular guide cannula, an introduction tube having a proximal end and a distal end and arranged so as to be insertable within the cannula, a flexible bar extending along and being displaceable within the tube, and a marking pin which is attached to a proximal end of the flexible bar and extends beyond the proximal end of the tube;

wherein the bar protrudes at the distal end of the introduction tube, the introduction tube together with the bar and the marking pin being arranged so as to be inserted into the guide cannula from a distal end of the cannula to place the proximal end of the introduction tube in the region of a proximal end of the guide cannula with the marking pin extending out of the proximal end of the guide cannula, a handle at the distal end of the introduction tube enabling the introduction tube to be guided and turned around its longitudinal axis, and the handle surrounds the distal end of the introduction tube and has a depression which is open on an edge and leads radially away from the introduction tube, the depression serving to receive the distal end of the bar.

26. A marker of a site on skeletal structure for a surgical procedure on a patient comprising:

a pin, and a driver constituting means for attaching the pin to the skeletal structure of the patient from outside of the patient through skin and flesh of the patient, the driver being engageable with the pin to provide an assembly, there being a distal end portion of the pin, wherein a proximal end of the pin is configured for attachment with the skeletal structure of the patient;

interface means between the pin and the driver for engaging the driver with the pin for transmission of motion from the driver to the pin for attaching the pin to the skeletal structure, the driver having a portion comprising means for being moved from the outside of the skin of the patient for initiating said motion of said driver for said transmission of the motion from the driver to said pin for said attachment; and the driver being disengagable from the pin by withdrawal of said driver in a condition of said attachment of the pin to the skeletal structure at the site of the surgical procedure, the driver being withdrawable from the skin and flesh of the patient, a distal end portion of the pin constituting means for extending to outside the patient through the skin and flesh of the patient, so as to serve as a marker subsequent to disengagement of the driver from the pin and withdrawal of said driver from the skin and flesh of the patient.

27. A marker for a surgical procedure according to claim 26, wherein said skeletal structure is a bone, a proximal end portion of said pin includes a screw thread for the attachment by screwing into the bone upon a rotation of said pin, and said interface means between said pin and said driver is configured for transmission of rotation from said driver to said pin.

28. A marker for a surgical procedure according to claim 26, further comprising a cannula of larger diameter than said assembly for receiving said assembly for guiding the assembly through the skin and flesh of the patient to adjacent to the site of the surgical procedure.

29. A marker for a surgical procedure according to claim 26, wherein said driver comprises a tube.

30. A marker for a surgical procedure according to claim 29, wherein said distal end portion is a wire which extends longitudinally through said tube.

31. A method for marking a surgical site on a bone of a surgical procedure comprising the steps of:

providing: X-rays, a cannula, a needle, an introduction tube, a marking pin with an elongated marker, and the elongated marker inserted into the introduction tube to provide with the marking pin and tube a tubular assembly with the pin operatively engaging the tube and extending beyond an end of the tube;

under observation with the X-rays, inserting the cannula through a patient's skin and flesh to adjacent the surgical site at the bone and inserting the needle through the cannula to the bone to impact upon the bone and create a score in the bone at the site;

retracting the needle from the cannula;

inserting the tubular assembly into the cannula and advancing the tubular assembly toward the bone to bring the pin in contact with the score on the bone with the elongated marker extending out of the cannula and skin;

operating the introduction tube for operating the tubular assembly to affix the pin to the bone; and retracting the cannula and the tube from the elongated marker and from the skin and flesh to leave the affixed pin in the bone and the elongated marker extending out of the skin as a marker of the site of the surgical procedure.

32. A method according to claim 31, wherein said step of inserting the cannula includes a step of orienting the cannula along an intended path of surgical incision and directed toward said site, and wherein the elongated marker lies substantially along the intended path of surgical incision, to mark the path.

33. A method according to claim 31, there being a screw thread on the pin for affixing the pin to the bone, said operating step comprising a rotating of the pin by rotation of the tube, there being mating surfaces between the tube and the pin so as to impart rotation of the tube to the pin.

34. The method according to claim 31, wherein the providing step provides the elongated marker as a flexible elongated marker.

35. The method according to claim 31, wherein the needle is a stylet.

36. A method of marking a surgical site of a surgical procedure upon a patient comprising the steps of:

providing a pin and a tube;

placing the pin in contact with an end of the tube to create a tubular assembly wherein a distal end portion of the pin extends into the tube and therebeyond and a proximal end of the pin is configured for engagement with skeletal structure of the patient, and wherein an interface between the pin and the tube is adapted for transmission of motion from the tube to the pin along an axis of the tube;

inserting the tubular assembly through the patient's skin and flesh to bring the proximal end of the pin in contact with the skeletal structure at the surgical site with the distal end portion of the pin extending out of the skin;

operating the tubular assembly to affix the pin to the skeletal structure; and retracting the tube from the pin and from the skin and flesh of the patient to leave the pin affixed to the skeletal structure and the distal end portion of the pin extending out of the skin as a marker of the site of the surgical procedure.

37. A method according to claim 36, wherein said operating of the tubular assembly comprises a step of rotating the tubular assembly about said axis, said transmission of motion includes transmission of rotation, and said skeletal structure is bone.

38. A method according to claim 36, further comprising providing a cannula, and inserting the cannula through the patient's skin and flesh toward the surgical site prior to said inserting of the tubular assembly and, wherein said step of inserting the tubular assembly is accomplished by passing the tubular assembly through the cannula.

39. The method according to claim 31, wherein said observation with X-rays comprises observation by fluoroscopy.

40. A marker of a site on a bone for a surgical procedure on a patient wherein the bone is inside a patient's skin and flesh, the marker comprising an external marker adapted to be located outside the skin of the patient, the external marker adapted to be directed towards the site on the bone of the patient and adapted to extend through the skin of the patient, and means for securing the external marker to the bone at the site at a desired angle of orientation of the external marker substantially along an intended path of surgical incision, wherein said securing means is adapted to cooperate with the bone and said marker is adapted to cooperate with the flesh and skin of the patient so as to maintain the desired angle of orientation of the external marker so as to provide a reliable indication of the site and of said angle.

* * * * *

UNITED STATES PATENT AND TRADEMARK OFFICE
CERTIFICATE OF CORRECTION

PATENT NO. : 5,665,092
DATED : September 9, 1997
INVENTOR(S) : Mangiardi et al.

It is certified that error appears in the above-identified patent and that said Letters Patent is hereby corrected as shown below:

On the cover page, [30], line 2, "Mar. 1, 1995" should read --Mar. 1, 1993 --.

Signed and Sealed this

Fifth Day of September, 2000

Attest:

Q. TODD DICKINSON

*Attesting Officer*  *Director of Patents and Trademarks*